US011865034B2

(12) United States Patent
Voorhees et al.

(10) Patent No.: US 11,865,034 B2
(45) Date of Patent: *Jan. 9, 2024

(54) MEDICAL PAD AND SYSTEM FOR THERMOTHERAPY

(71) Applicant: Medivance Incorporated, Louisville, CO (US)

(72) Inventors: Marc E. Voorhees, Arvada, CO (US); Michael R. Hoglund, Windsor, CO (US); Keir D. Hart, Lafayette, CO (US)

(73) Assignee: Medivance Incorporated, Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/589,849

(22) Filed: Jan. 31, 2022

(65) Prior Publication Data

US 2022/0151821 A1 May 19, 2022
US 2023/0077318 A9 Mar. 9, 2023

Related U.S. Application Data

(63) Continuation of application No. 16/597,393, filed on Oct. 9, 2019, now Pat. No. 11,234,859, which is a
(Continued)

(51) Int. Cl.
*A61F 7/00* (2006.01)
*A61F 7/10* (2006.01)
*A61F 7/08* (2006.01)

(52) U.S. Cl.
CPC ............... *A61F 7/00* (2013.01); *A61F 7/08* (2013.01); *A61F 7/10* (2013.01);
(Continued)

(58) Field of Classification Search
CPC .............. A61F 2007/0054; A61F 2007/0056
See application file for complete search history.

(56) References Cited

U.S. PATENT DOCUMENTS 2,250,325 A  7/1941  Barnes
2,595,328 A  5/1952  Bowen
(Continued)

FOREIGN PATENT DOCUMENTS

AU  2007201161 B2  12/2010
CA     2729122 A1   7/2002
(Continued)

OTHER PUBLICATIONS

Machine Translation of CN 102746512 A to Hirakawa (Year: 2012).*
(Continued)

*Primary Examiner* — Kaitlyn E Smith
(74) *Attorney, Agent, or Firm* — Rutan & Tucker LLP (57) ABSTRACT

An improved medical pad for contact thermal exchange with a patient includes a fluid circulation layer for containing a thermal exchange fluid circulatable therethrough, a first port and a second port for circulating the thermal exchange fluid in to and out of the fluid circulation layer, and a hydrogel layer interconnected to and extending across one side of the fluid circulation layer to define an adhesive surface for adherence to a patient's skin. The hydrogel layer can include an ultraviolet light-cured composition with a cross-linking copolymer, water, and glycerol. The hydrogel layer is provided to have a thermal conductivity of at least about 1.9 ca//hr-cm-° C.

19 Claims, 8 Drawing Sheets

Related U.S. Application Data continuation of application No. 15/035,062, filed as application No. PCT/US2016/015688 on Jan. 29, 2016, now Pat. No. 10,441,458.

(60) Provisional application No. 62/108,417, filed on Jan. 27, 2015.

(52) U.S. Cl.
CPC ............... *A61F 2007/0001* (2013.01); *A61F 2007/0054* (2013.01); *A61F 2007/0056* (2013.01); *A61F 2007/0086* (2013.01); *A61F 2007/0093* (2013.01); *A61F 2007/0096* (2013.01); *A61F 2007/0098* (2013.01)

(56) References Cited

U.S. PATENT DOCUMENTS

| | | |
|---|---|---|
| 2,602,302 A | 7/1952 | Poux |
| 2,726,658 A | 12/1955 | Chessey |
| 3,075,529 A | 1/1963 | Joseph, Jr. |
| 3,091,242 A | 5/1963 | Johnson, Jr. et al. |
| 3,212,286 A | 10/1965 | Curtis |
| 3,506,013 A | 4/1970 | Zdenek |
| 3,734,293 A | 5/1973 | Biskis |
| 3,830,676 A | 8/1974 | Elkins |
| 3,867,939 A | 2/1975 | Moore et al. |
| 3,900,035 A | 8/1975 | Welch et al. |
| 3,927,671 A | 12/1975 | Chittenden et al. |
| 3,995,621 A | 12/1976 | Fletcher et al. |
| 4,092,982 A | 6/1978 | Salem |
| 4,108,146 A | 8/1978 | Golden |
| 4,114,620 A | 9/1978 | Moore et al. |
| 4,118,946 A | 10/1978 | Tubin |
| 4,149,541 A | 4/1979 | Gammons et al. |
| 4,154,245 A | 5/1979 | Daily |
| 4,161,210 A | 7/1979 | Reid et al. |
| 4,195,631 A | 4/1980 | Baucom |
| 4,311,022 A | 1/1982 | Hall |
| 4,444,727 A | 4/1984 | Yanagihara et al. |
| 4,508,123 A | 4/1985 | Wyatt et al. |
| 4,580,408 A | 4/1986 | Stuebner |
| 4,753,241 A | 6/1988 | Brannigan et al. |
| 4,834,705 A | 5/1989 | Vaillancourt |
| 4,846,176 A | 7/1989 | Golden |
| 4,884,304 A | 12/1989 | Elkins |
| 4,886,063 A | 12/1989 | Crews |
| 4,908,248 A | 3/1990 | Nakashima et al. |
| 4,919,134 A | 4/1990 | Streeter |
| 4,962,761 A | 10/1990 | Golden |
| 4,981,135 A | 1/1991 | Hardy |
| 4,989,607 A | 2/1991 | Keusch et al. |
| 5,000,252 A | 3/1991 | Faghri |
| 5,005,374 A | 4/1991 | Spitler |
| 5,050,596 A | 9/1991 | Walasek et al. |
| 5,062,414 A | 11/1991 | Grim |
| 5,072,875 A | 12/1991 | Zacoi |
| 5,097,829 A | 3/1992 | Quisenberry |
| 5,111,668 A | 5/1992 | Parrish et al. |
| 5,113,666 A | 5/1992 | Parrish et al. |
| 5,133,348 A | 7/1992 | Mayn |
| 5,146,625 A | 9/1992 | Steele et al. |
| 5,190,032 A | 3/1993 | Zacoi |
| 5,265,669 A | 11/1993 | Schneider |
| 5,268,022 A | 12/1993 | Garrett et al. |
| 5,289,695 A | 3/1994 | Parrish et al. |
| 5,300,103 A | 4/1994 | Stempel et al. |
| 5,304,213 A | 4/1994 | Berke et al. |
| 5,304,216 A | 4/1994 | Wallace |
| 5,320,164 A | 6/1994 | Szczesuil et al. |
| 5,383,919 A | 1/1995 | Kelly et al. |
| 5,393,462 A | 2/1995 | Avery |
| 5,405,366 A | 4/1995 | Fox et al. |
| 5,407,421 A | 4/1995 | Goldsmith |
| 5,409,500 A | 4/1995 | Dyrek |
| 5,411,541 A | 5/1995 | Bell et al. |
| 5,423,751 A | 6/1995 | Harrison et al. |
| 5,456,701 A | 10/1995 | Stout |
| 5,466,250 A | 11/1995 | Johnson, Jr. et al. |
| 5,470,353 A | 11/1995 | Jensen |
| 5,484,448 A | 1/1996 | Steele et al. |
| 5,486,207 A | 1/1996 | Mahawili |
| 5,514,169 A | 5/1996 | Dickerhoff et al. |
| 5,545,194 A | 8/1996 | Augustine |
| 5,605,144 A | 2/1997 | Simmons et al. |
| 5,609,620 A | 3/1997 | Daily |
| 5,620,482 A | 4/1997 | Augustine et al. |
| 5,624,477 A | 4/1997 | Armond |
| 5,634,940 A | 6/1997 | Panyard |
| 5,640,728 A | 6/1997 | Graebe |
| 5,645,855 A | 7/1997 | Lorenz |
| 5,658,325 A | 8/1997 | Augustine |
| 5,662,695 A | 9/1997 | Mason et al. |
| 5,683,439 A | 11/1997 | Jensen |
| 5,720,774 A | 2/1998 | Glucksman |
| 5,733,318 A | 3/1998 | Augustine |
| 5,755,755 A | 5/1998 | Panyard |
| 5,785,716 A | 7/1998 | Bayron et al. |
| 5,806,335 A | 9/1998 | Herbert et al. |
| 5,824,025 A | 10/1998 | Augustine |
| 5,837,002 A | 11/1998 | Augustine et al. |
| 5,840,080 A | 11/1998 | Der Ovanesian |
| 5,843,145 A | 12/1998 | Brink |
| 5,871,526 A | 2/1999 | Gibbs et al. |
| 5,879,378 A | 3/1999 | Usui |
| 5,887,437 A | 3/1999 | Maxim |
| 5,913,849 A | 6/1999 | Sundstrom et al. |
| 5,948,012 A | 9/1999 | Mahaffey et al. |
| 5,968,000 A | 10/1999 | Harrison et al. |
| 5,986,163 A | 11/1999 | Augustine |
| 5,989,285 A | 11/1999 | DeVilbiss et al. |
| 6,010,528 A | 1/2000 | Augustine et al. |
| 6,019,783 A | 2/2000 | Philips et al. |
| 6,030,412 A | 2/2000 | Klatz et al. |
| 6,047,106 A | 4/2000 | Salyer |
| 6,074,415 A | 6/2000 | Der Ovanesian |
| 6,083,256 A | 7/2000 | Der Ovanesian |
| 6,083,418 A | 7/2000 | Czarnecki et al. |
| 6,117,164 A | 9/2000 | Gildersleeve et al. |
| 6,176,870 B1 | 1/2001 | Augustine |
| 6,185,744 B1 | 2/2001 | Poholski |
| 6,188,930 B1 | 2/2001 | Carson |
| 6,189,149 B1 | 2/2001 | Allen |
| 6,197,045 B1 | 3/2001 | Carson |
| 6,234,538 B1 | 5/2001 | Lauer |
| 6,238,427 B1 | 5/2001 | Matta |
| 6,257,011 B1 | 7/2001 | Siman-Tov et al. |
| 6,290,716 B1 | 9/2001 | Augustine |
| 6,336,935 B1 | 1/2002 | Davis et al. |
| 6,349,560 B1 | 2/2002 | Maier-Laxhuber et al. |
| 6,352,550 B1 | 3/2002 | Gildersleeve et al. |
| 6,364,937 B1 | 4/2002 | McMahon |
| 6,371,976 B1 | 4/2002 | Vrzalik et al. |
| 6,375,674 B1 * | 4/2002 | Carson ............... F28F 21/065 607/104 |
| 6,389,839 B1 | 5/2002 | Sabin |
| 6,436,130 B1 | 8/2002 | Philips et al. |
| 6,454,792 B1 | 9/2002 | Noda et al. |
| 6,461,379 B1 | 10/2002 | Carson et al. |
| 6,463,212 B1 | 10/2002 | Salyer |
| 6,503,297 B1 | 1/2003 | Lu et al. |
| 6,508,831 B1 | 1/2003 | Kushnir |
| 6,508,859 B1 | 1/2003 | Zia et al. |
| 6,511,501 B1 | 1/2003 | Augustine et al. |
| 6,511,502 B2 | 1/2003 | Fletcher |
| 6,517,510 B1 | 2/2003 | Stewart et al. |
| D471,987 S | 3/2003 | Hoglund et al. |
| D472,322 S | 3/2003 | Hoglund et al. |
| D474,544 S | 5/2003 | Hoglund et al. |
| 6,559,096 B1 | 5/2003 | Smith et al. |
| 6,584,797 B1 | 7/2003 | Smith et al. |
| 6,591,630 B2 | 7/2003 | Smith et al. |
| 6,601,404 B1 | 8/2003 | Roderick |
| 6,613,030 B1 | 9/2003 | Coles et al. |

(56) References Cited

U.S. PATENT DOCUMENTS

| | | |
|---|---|---|
| 6,620,187 B2 | 9/2003 | Carson et al. |
| 6,620,188 B1 | 9/2003 | Ginsburg et al. |
| 6,645,232 B2 | 11/2003 | Carson |
| 6,648,905 B2 | 11/2003 | Hoglund et al. |
| 6,653,607 B2 | 11/2003 | Ellis et al. |
| D483,125 S | 12/2003 | Hoglund et al. |
| 6,660,027 B2 | 12/2003 | Gruszecki et al. |
| 6,669,715 B2 | 12/2003 | Hoglund et al. |
| 6,682,525 B2 | 1/2004 | Lalonde et al. |
| D487,147 S | 2/2004 | Ellingboe et al. |
| D487,148 S | 2/2004 | Ellingboe et al. |
| 6,688,132 B2 | 2/2004 | Smith et al. |
| 6,692,518 B2 | 2/2004 | Carson |
| 6,699,267 B2 | 3/2004 | Voorhees et al. |
| 6,701,724 B2 | 3/2004 | Smith et al. |
| 6,743,250 B2 | 6/2004 | Renfro |
| 6,755,801 B2 | 6/2004 | Utterberg et al. |
| 6,755,852 B2 | 6/2004 | Lachenbruch et al. |
| D492,773 S | 7/2004 | Ellingboe et al. |
| 6,770,848 B2 | 8/2004 | Haas et al. |
| 6,799,063 B2 | 9/2004 | Carson |
| 6,800,087 B2 | 10/2004 | Papay et al. |
| 6,802,855 B2 | 10/2004 | Ellingboe et al. |
| 6,802,885 B2 | 10/2004 | Luk et al. |
| 6,818,012 B2 | 11/2004 | Ellingboe |
| 6,827,728 B2 | 12/2004 | Ellingboe et al. |
| 6,846,322 B2 | 1/2005 | Kane et al. |
| 6,858,068 B2 | 2/2005 | Smith et al. |
| 6,878,156 B1 | 4/2005 | Noda |
| 6,893,453 B2 | 5/2005 | Agarwal et al. |
| 6,904,956 B2 | 6/2005 | Noel |
| 6,909,074 B1 | 6/2005 | Bradley |
| 6,921,198 B2 | 7/2005 | Gruszecki et al. |
| 6,931,875 B1 | 8/2005 | Allen et al. |
| 6,942,644 B2 | 9/2005 | Worthen |
| 6,960,243 B1 | 11/2005 | Smith et al. |
| 6,968,711 B2 | 11/2005 | Smith et al. |
| 6,969,399 B2 | 11/2005 | Schock et al. |
| 7,008,445 B2 | 3/2006 | Lennox |
| 7,022,099 B2 | 4/2006 | Litzie et al. |
| 7,044,960 B2 | 5/2006 | Voorhees et al. |
| 7,052,509 B2 | 5/2006 | Lennox et al. |
| 7,055,575 B2 | 6/2006 | Noel |
| 7,056,335 B2 | 6/2006 | Agarwal et al. |
| 7,063,718 B2 | 6/2006 | Dobak, III |
| 7,077,858 B2 | 7/2006 | Fletcher et al. |
| 7,097,657 B2 | 8/2006 | Noda et al. |
| 7,101,389 B1 | 9/2006 | Augustine et al. |
| 7,122,047 B2 | 10/2006 | Grahn et al. |
| 7,160,316 B2 | 1/2007 | Hamilton et al. |
| 7,172,586 B1 | 2/2007 | Dae et al. |
| 7,240,720 B2 | 7/2007 | Noel |
| 7,303,554 B2 | 12/2007 | Lalonde et al. |
| 7,303,579 B2 | 12/2007 | Schock et al. |
| 7,338,516 B2 | 3/2008 | Quincy, III et al. |
| 7,361,186 B2 | 4/2008 | Voorhees et al. |
| 7,377,935 B2 | 5/2008 | Schock et al. |
| 7,507,250 B2 | 3/2009 | Lennox |
| 7,517,360 B2 | 4/2009 | Frey et al. |
| RE40,815 E | 6/2009 | Kudaravalli et al. |
| 7,547,320 B2 | 6/2009 | Schook et al. |
| RE40,868 E | 8/2009 | Ryba et al. |
| 7,621,944 B2 | 11/2009 | Wilson et al. |
| 7,621,945 B2 | 11/2009 | Lennox et al. |
| 7,666,213 B2 | 2/2010 | Freedman, Jr. et al. |
| 7,678,716 B2 | 3/2010 | Yahiaoui et al. |
| 7,686,840 B2 | 3/2010 | Quincy, III et al. |
| 7,727,228 B2 | 6/2010 | Abboud et al. |
| 7,731,739 B2 | 6/2010 | Schock et al. |
| 7,744,640 B1 | 6/2010 | Faries, Jr. et al. |
| 7,763,061 B2 | 7/2010 | Schorr et al. |
| 7,771,461 B2 | 8/2010 | Schock et al. |
| 7,784,304 B2 | 8/2010 | Trinh et al. |
| 7,799,063 B2 | 9/2010 | Ingram et al. |
| 7,827,815 B2 | 11/2010 | Carson et al. |
| 7,867,266 B2 | 1/2011 | Collins |
| 7,892,269 B2 | 2/2011 | Collins et al. |
| 7,896,910 B2 | 3/2011 | Schirrmacher et al. |
| 7,918,243 B2 | 4/2011 | Diodati et al. |
| 8,047,010 B2 | 11/2011 | Carson et al. |
| 8,052,624 B2 | 11/2011 | Buchanan et al. |
| 8,066,752 B2 | 11/2011 | Hamilton et al. |
| 8,182,521 B2 | 5/2012 | Kane et al. |
| 8,187,697 B2 | 5/2012 | Quincy, III et al. |
| 8,283,602 B2 | 10/2012 | Augustine et al. |
| 8,454,671 B2 | 6/2013 | Lennox et al. |
| D685,916 S | 7/2013 | Hoglund |
| 8,491,644 B1 | 7/2013 | Carson et al. |
| 8,597,217 B2 | 12/2013 | Lowe et al. |
| 8,603,150 B2 | 12/2013 | Kane et al. |
| 8,632,576 B2 | 1/2014 | Quisenberry |
| 8,647,374 B2 | 2/2014 | Koewler |
| 8,715,330 B2 | 5/2014 | Lowe et al. |
| 8,778,119 B2 | 7/2014 | Starr et al. |
| 8,808,344 B2 | 8/2014 | Scott et al. |
| 9,034,458 B2 | 5/2015 | Li |
| 9,078,742 B2 | 7/2015 | Quincy, III et al. |
| 9,089,462 B1 | 7/2015 | Lafleche |
| 9,211,358 B2 | 12/2015 | Sinko et al. |
| 9,278,024 B2 | 3/2016 | Scott et al. |
| 9,333,112 B2 | 5/2016 | Carson |
| 9,552,706 B2 | 1/2017 | Schneider, II et al. |
| 9,566,185 B2 | 2/2017 | Carson et al. |
| 9,622,907 B2 | 4/2017 | Carson et al. |
| 9,687,386 B2 | 6/2017 | Carson |
| 9,763,823 B2 | 9/2017 | Voorhees et al. |
| 9,907,889 B2 | 3/2018 | Locke et al. |
| 10,123,902 B2 | 11/2018 | Carson et al. |
| 10,220,198 B2 | 3/2019 | Fuchs et al. |
| 10,258,501 B2 | 4/2019 | Carson |
| 10,441,458 B2 * | 10/2019 | Voorhees ............... A61F 7/08 |
| 10,441,707 B2 | 10/2019 | Voorhees et al. |
| 10,548,778 B2 | 2/2020 | Hassenpflug et al. |
| 11,234,859 B2 * | 2/2022 | Voorhees ............... A61F 7/10 |
| 2002/0015689 A1 | 2/2002 | Munro et al. |
| 2002/0111657 A1 | 8/2002 | Dae et al. |
| 2002/0138121 A1 | 9/2002 | Fox |
| 2002/0161419 A1 | 10/2002 | Carson et al. |
| 2003/0074038 A1 | 4/2003 | Gruszecki et al. |
| 2003/0078638 A1 | 4/2003 | Voorhees et al. |
| 2003/0078639 A1 | 4/2003 | Carson |
| 2003/0078640 A1 | 4/2003 | Carson et al. |
| 2003/0109911 A1 | 6/2003 | Lachenbruch et al. |
| 2003/0114903 A1 | 6/2003 | Ellingboe |
| 2003/0135252 A1 | 7/2003 | MacHold et al. |
| 2003/0149359 A1 | 8/2003 | Smith |
| 2003/0149461 A1 | 8/2003 | Johnson |
| 2003/0150232 A1 | 8/2003 | Brudnicki |
| 2003/0163179 A1 | 8/2003 | Hoglund et al. |
| 2003/0163180 A1 | 8/2003 | Hoglund et al. |
| 2003/0163183 A1 | 8/2003 | Carson |
| 2003/0163185 A1 | 8/2003 | Carson |
| 2003/0212416 A1 | 11/2003 | Cinelli et al. |
| 2004/0030372 A1 | 2/2004 | Ellingboe et al. |
| 2004/0030373 A1 | 2/2004 | Ellingboe et al. |
| 2004/0059212 A1 | 3/2004 | Abreu |
| 2004/0064170 A1 | 4/2004 | Radons et al. |
| 2004/0073280 A1 | 4/2004 | Dae et al. |
| 2004/0082886 A1 | 4/2004 | Timpson |
| 2004/0087606 A1 | 5/2004 | Voorhees et al. |
| 2004/0133253 A1 | 7/2004 | Grahn et al. |
| 2004/0225341 A1 | 11/2004 | Schock et al. |
| 2004/0243122 A1 | 12/2004 | Auth et al. |
| 2004/0252750 A1 | 12/2004 | Gruszecki et al. |
| 2004/0260369 A1 | 12/2004 | Schock et al. |
| 2004/0267339 A1 | 12/2004 | Yon et al. |
| 2005/0060012 A1 | 3/2005 | Voorhees et al. |
| 2005/0065583 A1 | 3/2005 | Voorhees et al. |
| 2005/0096714 A1 | 5/2005 | Freedman et al. |
| 2005/0177212 A1 | 8/2005 | Njemanze |
| 2005/0187502 A1 | 8/2005 | Krempel et al. |
| 2005/0244629 A1 | 11/2005 | Usui et al. |
| 2005/0288749 A1 | 12/2005 | Lachenbruch |
| 2006/0024053 A1 | 2/2006 | Grant |

(56) References Cited

U.S. PATENT DOCUMENTS

| | | |
|---|---|---|
| 2006/0030916 A1 | 2/2006 | Lennox |
| 2006/0036304 A1 | 2/2006 | Cordani et al. |
| 2006/0058858 A1 | 3/2006 | Smith |
| 2006/0074469 A1 | 4/2006 | Lennox et al. |
| 2006/0122673 A1 | 6/2006 | Callister et al. |
| 2006/0124141 A1 | 6/2006 | Dobak |
| 2006/0136023 A1 | 6/2006 | Dobak |
| 2006/0161232 A1 | 7/2006 | Kasza et al. |
| 2006/0190066 A1 | 8/2006 | Worthen |
| 2006/0235114 A1 | 10/2006 | Kitazono et al. |
| 2006/0247744 A1 | 11/2006 | Nest et al. |
| 2006/0276089 A1 | 12/2006 | Amarasinghe et al. |
| 2006/0287697 A1 | 12/2006 | Lennox |
| 2006/0293734 A1 | 12/2006 | Scott et al. |
| 2007/0043409 A1 | 2/2007 | Brian et al. |
| 2007/0049997 A1 | 3/2007 | Fields et al. |
| 2007/0054122 A1 | 3/2007 | Paisner et al. |
| 2007/0068931 A1 | 3/2007 | Augustine et al. |
| 2007/0100404 A1 | 5/2007 | Ko et al. |
| 2007/0173735 A1 | 7/2007 | Callister et al. |
| 2007/0213793 A1 | 9/2007 | Hayes |
| 2007/0225782 A1 | 9/2007 | Taylor |
| 2007/0244475 A1 | 10/2007 | Carson et al. |
| 2007/0270925 A1 | 11/2007 | Levinson |
| 2008/0027523 A1 | 1/2008 | Behringer et al. |
| 2008/0046046 A1 | 2/2008 | Ginsburg |
| 2008/0114431 A1 | 5/2008 | Ginsburg |
| 2008/0147152 A1 | 6/2008 | Quincy et al. |
| 2008/0249524 A1 | 10/2008 | Dunning |
| 2008/0255644 A1 | 10/2008 | Carson |
| 2008/0275534 A1 | 11/2008 | Noel |
| 2009/0018504 A1 | 1/2009 | Pile-Spellman et al. |
| 2009/0043366 A1 | 2/2009 | Dae |
| 2009/0088825 A1 | 4/2009 | Ota |
| 2009/0099629 A1 | 4/2009 | Carson et al. |
| 2009/0131835 A1 | 5/2009 | Voorhees et al. |
| 2009/0157000 A1 | 6/2009 | Waller |
| 2009/0177184 A1 | 7/2009 | Christensen et al. |
| 2009/0182400 A1 | 7/2009 | Dae et al. |
| 2009/0250367 A1 | 10/2009 | Murdoch et al. |
| 2009/0280182 A1 | 11/2009 | Beck et al. |
| 2009/0287283 A1 | 11/2009 | Biser et al. |
| 2009/0299287 A1 | 12/2009 | Carson et al. |
| 2009/0312823 A1 | 12/2009 | Patience et al. |
| 2009/0326619 A1 | 12/2009 | Kagan |
| 2010/0016933 A1 | 1/2010 | Chen et al. |
| 2010/0168825 A1 | 7/2010 | Barbknecht |
| 2010/0198122 A1 | 8/2010 | Freund |
| 2010/0198320 A1 | 8/2010 | Pierre et al. |
| 2010/0204765 A1 | 8/2010 | Hall et al. |
| 2011/0021960 A1 | 1/2011 | Filtvedt et al. |
| 2011/0029051 A1 | 2/2011 | Ross |
| 2011/0045056 A1 | 2/2011 | Munro et al. |
| 2011/0125238 A1 | 5/2011 | Nofzinger |
| 2011/0166633 A1 | 7/2011 | Stull |
| 2011/0172749 A1 | 7/2011 | Christensen et al. |
| 2011/0306972 A1 | 12/2011 | Widenhouse et al. |
| 2011/0307040 A1 | 12/2011 | Peterson |
| 2011/0308781 A1 | 12/2011 | O'Riordan et al. |
| 2011/0313497 A1 | 12/2011 | McFarlane |
| 2012/0046720 A1 | 2/2012 | Ishizaki |
| 2012/0065715 A1 | 3/2012 | Carson |
| 2012/0080031 A1 | 4/2012 | Belson |
| 2012/0095536 A1 | 4/2012 | Machold et al. |
| 2012/0185021 A1 | 7/2012 | Johnson et al. |
| 2012/0191035 A1 | 7/2012 | Stephan |
| 2012/0220960 A1 | 8/2012 | Ruland |
| 2013/0116760 A1 | 5/2013 | Carson et al. |
| 2013/0238042 A1 | 9/2013 | Gildersleeve et al. |
| 2014/0039451 A1 | 2/2014 | Bangera et al. |
| 2014/0172050 A1 | 6/2014 | Dabrowiak |
| 2014/0214138 A1 | 7/2014 | Voorhees et al. |
| 2014/0277301 A1 | 9/2014 | Varga et al. |
| 2014/0316494 A1 | 10/2014 | Augustine et al. |
| 2014/0343639 A1 | 11/2014 | Hopper et al. |
| 2015/0051673 A1 | 2/2015 | Rivas Tapia |
| 2015/0223972 A1 | 8/2015 | Dabrowiak |
| 2015/0230973 A1 | 8/2015 | Dabrowiak et al. |
| 2015/0250643 A1 | 9/2015 | Paradis |
| 2015/0290042 A1 | 10/2015 | Freer et al. |
| 2015/0373781 A1 | 12/2015 | Augustine et al. |
| 2016/0008166 A1 | 1/2016 | Voorhees et al. |
| 2016/0038336 A1 | 2/2016 | Hilton et al. |
| 2016/0324683 A1 | 11/2016 | Carson |
| 2017/0049618 A1 | 2/2017 | Ward et al. |
| 2017/0151087 A1 | 6/2017 | Carson et al. |
| 2017/0189225 A1 | 7/2017 | Voorhees et al. |
| 2017/0224528 A1 | 8/2017 | Berg et al. |
| 2017/0246029 A1 | 8/2017 | Clark |
| 2017/0246031 A1 | 8/2017 | Benyaminpour et al. |
| 2017/0246374 A1 | 8/2017 | Voorhees et al. |
| 2017/0348144 A1 | 12/2017 | Taylor et al. |
| 2017/0348145 A1 | 12/2017 | Voorhees et al. |
| 2017/0354534 A1 | 12/2017 | Paradis et al. |
| 2018/0042762 A1 | 2/2018 | Galer |
| 2018/0207024 A1 | 7/2018 | Dabrowiak et al. |
| 2018/0214297 A1 | 8/2018 | Hughett et al. |
| 2018/0214302 A1 | 8/2018 | Dabrowiak et al. |
| 2019/0085644 A1 | 3/2019 | Ames et al. |
| 2019/0117446 A1 | 4/2019 | Carson et al. |
| 2020/0071051 A1 | 3/2020 | Lewis |
| 2020/0155341 A1 | 5/2020 | Voorhees et al. |
| 2022/0087874 A1 | 3/2022 | Schneider et al. |
| 2022/0192865 A1 | 6/2022 | Hughett, Sr. et al. |
| 2022/0192867 A1 | 6/2022 | Stich et al. |
| 2022/0233344 A1 | 7/2022 | Hoglund |
| 2022/0233347 A1 | 7/2022 | Canary et al. |
| 2022/0265468 A1 | 8/2022 | Xu et al. |
| 2022/0280336 A1 | 9/2022 | Smith et al. |
| 2022/0287875 A1 | 9/2022 | Minchew et al. |
| 2022/0287876 A1 | 9/2022 | Smith et al. |
| 2022/0296413 A1 | 9/2022 | Jones |
| 2022/0296414 A1 | 9/2022 | Bible et al. |
| 2022/0304847 A1 | 9/2022 | Kuroda et al. |
| 2022/0313478 A1 | 10/2022 | Johnston et al. |
| 2022/0347009 A1 | 11/2022 | Hughett, Sr. et al. |
| 2022/0401259 A1 | 12/2022 | Basciano et al. |
| 2023/0000668 A1 | 1/2023 | Walker et al. |
| 2023/0009524 A1 | 1/2023 | Johnston et al. |
| 2023/0011631 A1 | 1/2023 | Yin et al. |
| 2023/0019048 A1 | 1/2023 | Stich et al. |
| 2023/0021245 A1 | 1/2023 | Walker et al. |
| 2023/0040583 A1 | 2/2023 | Falis et al. |

FOREIGN PATENT DOCUMENTS

| | | | |
|---|---|---|---|
| CN | 102026596 A | 4/2011 | |
| CN | 101389372 B | 8/2012 | |
| CN | 102746518 A | * 10/2012 | ............ A61L 15/60 |
| CN | 103939695 B | 3/2016 | |
| EP | 1641503 A2 | 4/2006 | |
| EP | 1718894 B1 | 7/2010 | |
| EP | 2204150 A1 | 7/2010 | |
| JP | H09-508045 A | 8/1997 | |
| JP | H09508045 A | 8/1997 | |
| JP | 2002-534160 A | 10/2002 | |
| JP | 2007029638 A | 2/2007 | |
| JP | 2013248293 A | 12/2013 | |
| WO | 98/31310 A1 | 7/1998 | |
| WO | 199944552 A1 | 9/1999 | |
| WO | 2000040185 A1 | 7/2000 | |
| WO | 2003086253 A2 | 10/2003 | |
| WO | 2005117546 A2 | 12/2005 | |
| WO | 2009/090403 A1 | 7/2009 | |
| WO | 2017/127768 A1 | 7/2017 | |
| WO | 2022/159879 A1 | 7/2022 | |
| WO | 2022/165068 A1 | 8/2022 | |

OTHER PUBLICATIONS

PCT/US2016/015688 filed Jan. 29, 2016 International Search Report and Written Opinion dated Apr. 1, 2016.

(56) References Cited

OTHER PUBLICATIONS

PCT/US2015/045548 filed Aug. 17, 2015 International Search Report and Written Opinion dated Nov. 24, 2015.
U.S. Appl. No. 15/512,025, filed Mar. 16, 2017 Final Office Action dated Jun. 25, 2020.
U.S. Appl. No. 15/512,025, filed Mar. 16, 2017 Non-Final Office Action dated Jul. 18, 2019.
Murray, R. Z., et al. "Development and use of biomaterials as wound healing therapies" Burns & Trauma (2019) 7:2 https://doi.org/10.1186/s41038-018-0139-7 (2019).
PCT/US2022/013672 filed Jan. 25, 2022, International Search Report and Written Opinion dated Jul. 15, 2022.
PCT/US2022/014147 filed Jan. 27, 2022 International Search Report and Written Opinion dated Jul. 18, 2022.
Sevgi, M., et al. "Topical Antimicrobials for Burn Infections—An Update" Recent Pat Antiinfect Drug Discov. Dec. 2013 ; 8(3): 161-197.
Stoica, A. E., et al. "Hydrogel Dressings for the Treatment of Burn Wounds: An Up-To-Date Overview" Materials 2020, 13, 2853; doi:10.3390/ma13122853. (2020).
Advantage Engineering, "Proper Use of Inhibited Propylene Glycol", Jun. 12, 2001, http://www.ttequip.com/knowledgelibrary/Proper%20Use%20Of%20Inh-ibited%20Propylene%20Glycol.pdf Jun. 12, 2001.
Hyperphysicis, "Thermal Conductivity", available Jul. 31, 2010, https://web.archive.org/web/20100731025127/http://hyperphysics.phy-astr.g- us.edu/hbase/tables.thrcn.html Jul. 31, 2010.
U.S. Appl. No. 16/597,393, filed Oct. 9, 2019 Corrected Notice of Allowability dated Nov. 18, 2021.
U.S. Appl. No. 16/597,393, filed Oct. 9, 2019 Non-Final Office Action dated Apr. 28, 2021.

\* cited by examiner

MEDICAL PAD AND SYSTEM FOR THERMOTHERAPY

CROSS-REFERENCE TO RELATED APPLICATIONS

This application is a continuation of U.S. patent application Ser. No. 16/597,393, filed Oct. 9, 2019, now U.S. Pat. No. 11,234,859, which is a continuation of U.S. patent application Ser. No. 15/035,062, filed May 6, 2016, now U.S. Pat. No. 10,441,458, which is a U.S. National Stage of International Patent Application No. PCT/US2016/015688, filed Jan. 29, 2016, which claims the benefit of priority to U.S. Provisional Application No. 62/108,417, filed Jan. 27, 2015, each of which is incorporated by reference in its entirety into this application.

FIELD OF INVENTION

The present invention relates an improved medical pad and system for use in patient temperature control, and in particular, for therapeutic patient temperature cooling to induce hypothermia and optionally patient warming to achieve normothermia.

BACKGROUND OF THE INVENTION

There are a number of medical conditions for which systemic cooling is an effective therapy. For example, rapid systemic cooling of stroke, head-trauma, cardiac arrest, and myocardial infarction patients has significant therapeutic benefits.

In that regard, stroke is a major cause of neurological disability, but research has established that even though a stroke victim's brain cells may lose their ability to function during the stroke, they do not necessarily die quickly. Brain damage resulting from a stroke may take hours to reach a maximum level. Neurological damage may be limited and the stroke victim's outcome improved if a cooling neuroprotectant therapy is applied during that timeframe.

Similar possibilities exist with victims of trauma, such as may result from vehicle crashes, falls, and the like. Such trauma may impart brain injury through mechanisms that have overlap with elements in the genesis of neurologic damage in stroke victims. Delayed secondary injury at the cellular level after the initial head trauma event is recognized as a major contributing factor to the ultimate tissue loss that occurs after brain injury.

Further, corresponding possibilities exist with cardiac arrest and myocardial infarction patients. Again, rapid cooling of such patients may limit neurological damage. In addition, rapid cooling may provide cardio protection. Further in that regard, rapid heart cooling of myocardial arrest patients prior to reperfusion procedures (e.g., carotid stenting) may significantly reduce reperfusion-related injuries.

Additionally, patients having a neurological disease may often have accompanying fever. Cooling such patients has been recently proposed to yield therapeutic benefits, but may entail cooling over an extended period of time.

Various approaches have been developed for applying cooling therapy. In one non-invasive approach, one or more contact pad(s) may be placed on a patient's body (e.g. the torso and/or legs of a patient) and a cooled fluid, such as cooled water or air, circulated through the pad(s). In turn, thermal energy is exchanged between the patient and the circulated fluid to cool the patient.

SUMMARY OF THE INVENTION

An objective of the present invention is to provide a medical pad for thermal exchange with a patient that facilitates the realization of pad production efficiencies and the reduction of pad production facility requirements.

Another objective of the present invention is to provide a medical pad for thermal exchange with a patient yields rapid thermal exchange with a patient.

A further objective of the present invention is to provide a medical pad for thermal exchange with a patient that provides stable mechanical properties to facilitate continued use on a patient over an extended time period.

An additional objective of the present invention is to provide a medical pad for thermal exchange with a patient that is bio-compatible and otherwise comfortable.

Yet a further objective of the present invention is to provide a medical pad for thermal exchange with a patient that is relatively easy to remove and does not require extensive hygienic patient clean-up after removal.

In one embodiment, an improved medical pad for contact and thermal exchange with a patient comprises a fluid circulation layer for containing a thermal exchange fluid circulatable therethrough, a first port fluidly interconnected to the fluid circulation layer for circulating the fluid into the fluid circulation layer, and a second port fluidly interconnected to the fluid circulation layer for circulating the fluid out of the fluid circulation layer. Further, the medical pad includes a hydrogel layer interconnected to and extending across one side of the fluid circulation layer to define an adhesive surface for adherence to a patient's skin.

Uniquely, the hydrogel layer comprises an ultra violet light-cured composition that includes a cross-linking copolymer in an amount of between about 15% to 30% by weight of the composition, and preferably in an amount of between about 25% to 30% by weight of the composition; water in an amount of between about 15% to 40% by weight of the composition, and preferably in an amount of between about 25% to 35% by weight of the composition; and glycerol in an amount of between about 25% to 35% by weight of the composition, and preferably in an amount of between about 27.5% to 32.5% by weight of the composition. Surprisingly, the water content utilized in the hydrogel layer facilitates the utilization of ultra violet light-cured compositions for facility-friendly and production-scale manufacturing, while also yielding a hydrogel layer having desirable mechanical properties, i.e. desirable degrees of thermal conductivity, shelf life stability, and tack strength.

In some embodiments, the hydrogel layer may be provided to have a thermal conductivity of at least about 1.9 cal/hr-cm-° C. More particularly, the hydrogel layer may have a thermal conductivity of between about 1.9 cal/hr-cm-° C. and 2.37 cal/hr-cm-° C.

In some implementations, the adhesive surface of the hydrogel layer may be provided to have a tack strength of between about 20 g and 65 g, as determined according to ISO 9665:1998(E).

In contemplated embodiments, the hydrogel layer may have a thickness of between about 0.018" and 0.04". More particularly, the hydrogel layer may have a thickness of between about 0.022" and 0.032".

Further, in contemplated embodiments, the fluid circulation layer may define an internal volume having an average or substantially equal geometric height, or thickness, across the fluid circulation layer of at least about 0.06", and preferably between about 0.06" and 0.1". In medical pad applications where fluid is circulated, or drawn, through the fluid circulation layer at a negative pressure, the fluid containing layer may have an effective internal volume height of between about 0.04" and 0.08" during circulated fluid flow therethrough.

In contemplated arrangements, the fluid circulation layer may comprise a flexible film layer and a flexible base member interconnected to the film layer for containing the circulatable thermal exchange fluid therebetween. In such arrangements, the hydrogel layer may have a thermal conductivity as indicated above.

In a system embodiment for contact thermal exchange with a patient, a medical pad having a fluid circulation layer, a hydrogel layer, and optional additional features as described above may be employed in combination with a controller and a fluid conditioning assembly that is fluidly interconnectable to an inlet port and outlet port of the pad. The fluid conditioning assembly may include a fluid pump for circulating a thermal exchange fluid through the pad and a heat exchanger for use in controlling a temperature of the circulated fluid (e.g. for cooling and optionally rewarming the cooled fluid). In the later regard, the controller may provide output signals for controlling operation of the heat exchanger to provide for temperature control of the circulated thermal exchange fluid in a predetermined manner.

In system embodiments, a patient temperature sensor may be provided for sensing a patient temperature (e.g. a patient core body temperature) and providing a patient temperature signal indicative thereof, wherein the controller may be provided to utilize the patient temperature signal in providing the output signals to the heat exchanger. Further, the fluid conditioning assembly may include a fluid temperature sensor for sensing the temperature of the circulated thermal exchange fluid and for providing a fluid temperature signal indicative thereof, wherein the controller may be provided to utilize the fluid temperature signal in providing the output signals to the heat exchanger.

Additional features and advantages will be recognized by those skilled in the art upon consideration of the further description that follows.

DETAILED DESCRIPTION

Figure 1:
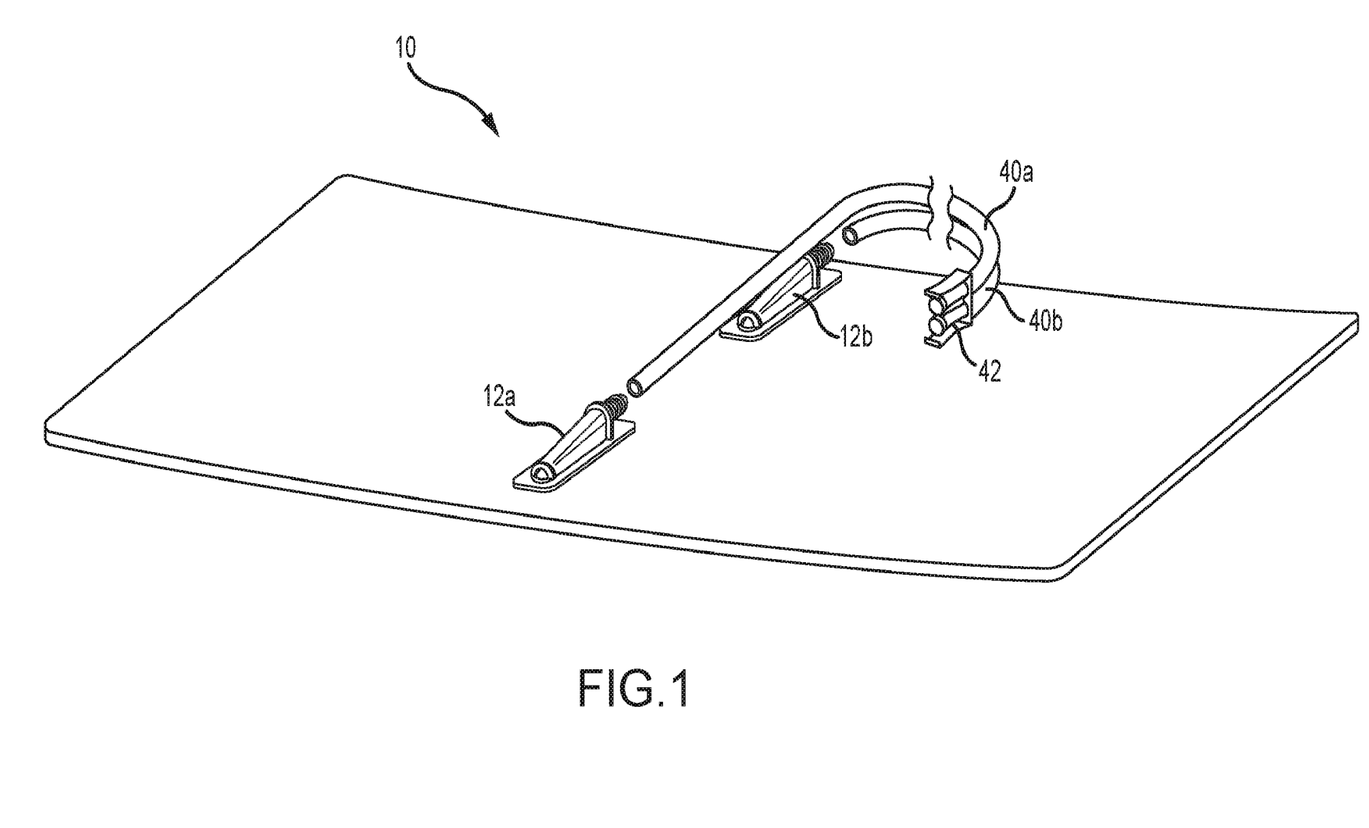
FIG. 1 is a perspective view of a medical pad embodiment.

One embodiment of a medical pad 10 for contact and thermal exchange with a skin region of a patient is illustrated in FIGS. 1-4. As shown in FIG. 1, the pad 10 may include an inlet port 16a and an outlet port 16b for circulating a thermal exchange fluid (e.g. a liquid such as water) in to and out of a fluid circulation layer of the pad 10. For such purposes, the inlet port 12a and outlet port 12b may have corresponding first ends that fluidly communicate with the fluid containing layer of the pad 10, respectively. The inlet port 12a and outlet port 12b may further include corresponding second ends that extend laterally outside of the fluid containing layer in a common direction. As illustrated, the second ends of inlet port 12a and outlet port 12b may be provided for fixed interconnection with fluid circulation lines 40a and 40b, respectively. In one approach, the fluid circulation lines 40a and 40b may be defined by lengths of flexible tubing. The fluid circulation lines 40a, 40b may be provided with a connector 42 for use in selective interconnection to and disconnection from a fluid conditioning assembly, wherein a thermal exchange fluid may be circulated through the pad 10, as will be further described hereinbelow.

Figure 2:
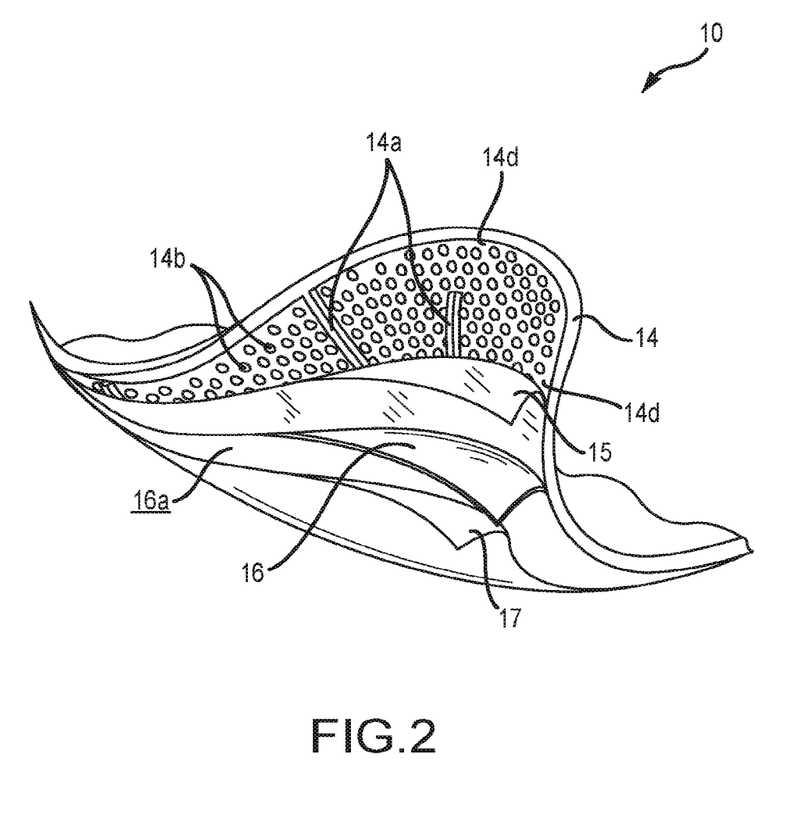
FIG. 2 is a perspective view of a corner of the medical pad embodiment of FIG. 1 with various layers of the medical pad embodiment separated for purposes of illustration.
Figure 3:
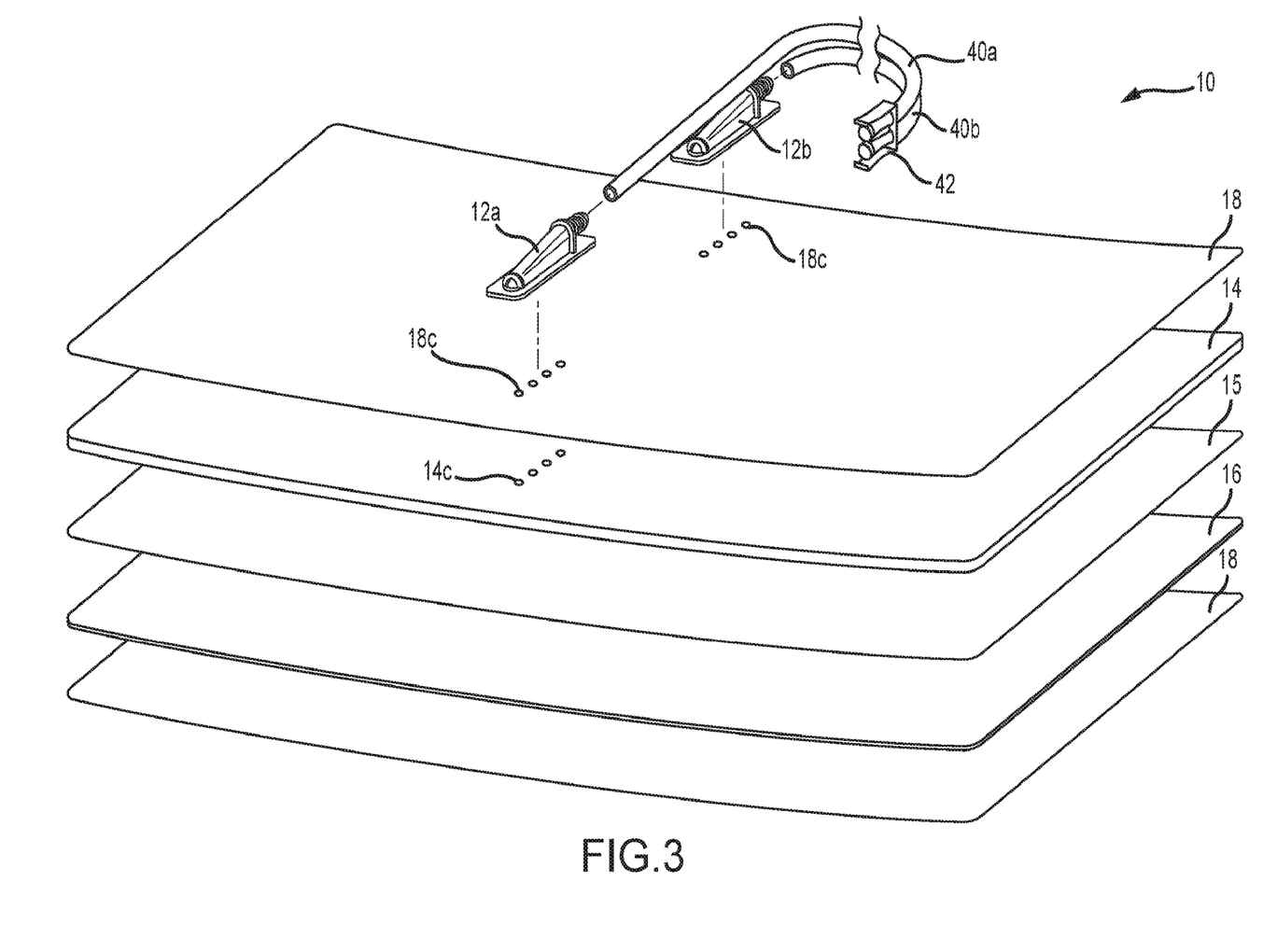
FIG. 3 is a perspective exploded view of the medical pad embodiment of FIG. 1.
Figure 4:
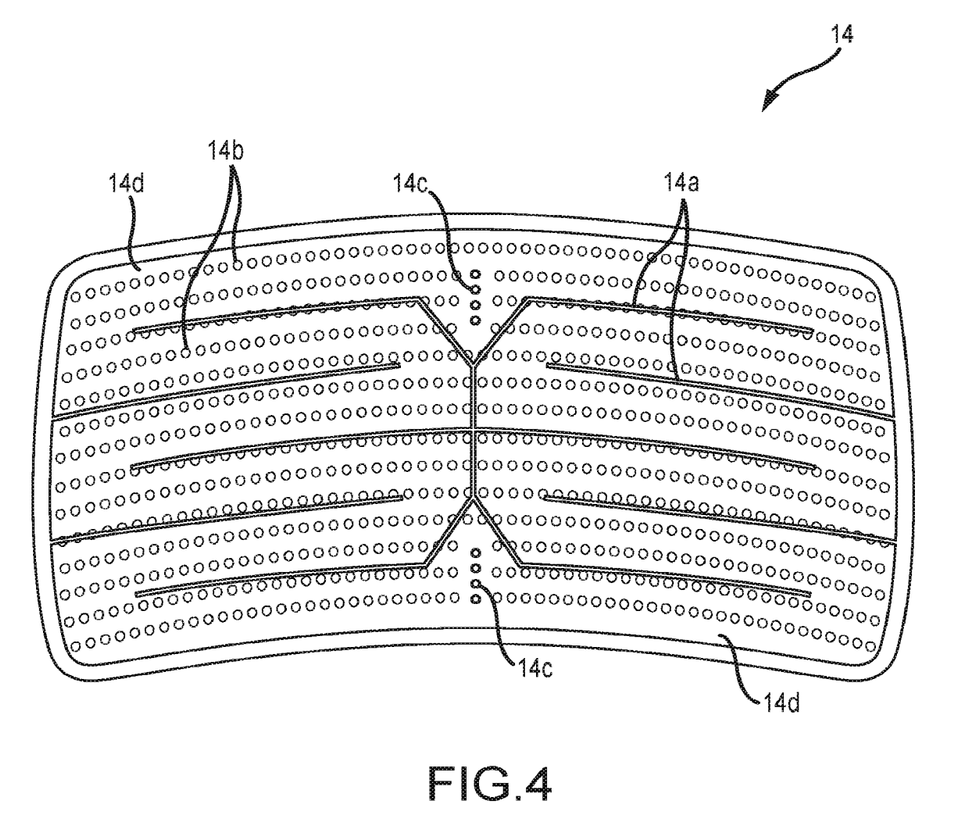
FIG. 4 is a bottom view of a base member of the medical pad embodiment of FIG. 1.

As best illustrated in FIGS. 2-4, the pad 10 may include a flexible base member 14 and a flexible film layer 15 that are interconnected to define the fluid circulation layer of pad 10, wherein the fluid circulation layer has an internal volume between the base member 14 and film layer 15. Further, pad 10 may comprise a flexible hydrogel layer 16 interconnected to the film layer 15. As will be further described, the hydrogel layer 16 provides for thermal conduction between the circulated thermal exchange fluid and a patient, and further presents an adhesive surface 16a to establish and maintain intimate contact with a skin region of a patient so as to optimize thermal exchange. The hydrogel layer may extend across a portion, a majority, or substantially the entirety of one side of the fluid circulation layer.

A removable liner layer 17 may be provided to cover the adhesive surface 16a prior to use. Further, an optional outer layer 18 may be provided on another side of the fluid containing layer.

As illustrated in FIGS. 2 and 4, the base member 14 may have two sets of one or more holes 14c extending therethrough, wherein one set is disposed in aligned relation with inlet port 12a and the other set is disposed in aligned relation with outlet port 12b. Similarly, optional layer 18 may have two sets of one or more holes 18c extending therethrough, wherein one set is disposed in aligned relation with inlet port 12a and the other set is disposed in aligned relation with outlet port 12b. In turn, circulated fluid may flow from inlet port 12a through the first sets of the holes and into the fluid circulation layer, then out of the fluid containment layer via the second sets of holes and outlet port 12b.

As shown in FIGS. 2 and 4, the fluid circulation layer may comprise one or a plurality of fluid channels to direct fluid flow between the inlet port 12a and outlet port 12b. In that regard, the base member 14 may include one or a plurality of rib members 14a that project from a base portion 14d and are interconnected to the film layer 15. The fluid channels may extend between adjacent rib members 14a and/or between sealed edges of the pad 10 and/or between rib members 14a and sealed edges of the pad 10.

The fluid channels may be configured to provide for fluid flow across the lateral extent of the pad 10. In some embodiments, the inlet port 12a and fluid channels may be spaced to define a staging region within the fluid containing layer that is adjacent to and fluidly interconnected to a first end of each of a plurality of channels. Further, the outlet port 12b and fluid channels may be spaced to define another staging region within the fluid containing layer that is adjacent to and fluidly interconnected to a second end of each of a plurality of channels.

The rib members 14a may be provided to project from the base portion 14d a distance that defines a geometric height, or thickness, of the internal volume of the fluid circulation layer. As may be appreciated, the rib members 14a may be provided to not only define fluid channels but also to support the film layer 15.

In the later regard, the base member 14 may also comprise a plurality of offset projections 14b that project from the base portion 14d a distance that is substantially the same or different from the projection distance of rib members 14a. In contemplated arrangements, the rib members 14a and projections 14b all may projection the same distance from base portion 14d, wherein the common distance is between about 0.06" to 0.10" from base portion 14d. As such, an internal volume having a geometric height, or thickness, of between about 0.06" and 0.10" is provided. In turn, medical pad applications where fluid is circulated, or drawn, through the fluid circulation layer at a negative pressure, the fluid containing layer may maintain an effective internal volume height of at least between about 0.04" and 0.08" during circulated fluid flow therethrough. In short, the rib members 14a and projections 14b may be provided to supportably engage the film layer 15 to define and maintain fluid flow passageways through the fluid circulation layer by keeping the film layer 15 from collapsing across the base member 14.

The hydrogel layer 16 may comprise an ultra violet light-cured composition that includes a cross-linking copolymer in an amount between about 15% to 30% by weight of the composition, and preferably in an amount between about 25% to 30% by weight of the composition; water in an amount between about 15% to 40% by weight of the composition, and preferably in an amount of between about 25% to 35% by weight of the composition; and glycerol in an amount between about 25% to 35% by weight of the composition, and preferably in an amount of between about 27.5% to 32.5% by weight of the composition. Further, the composition may comprise potassium chloride, e.g. in an amount between about 1.75% to 2.25% by weight of the composition, and/or (poly)vinyl pyrrolidone, e.g. in an amount between about 1.25% to 1.75% by weight of the composition.

In one implementation, the hydrogel layer 16 may comprise an ultraviolet light-cured composition having a formulation as set forth in Table 1 below.

TABLE 1

| Material | Percentage by Weight |
|---|---|
| Glycerin | 30 ± .25% |
| Water | 34 ± .25% |
| NaAMPS*/AA co-polymer | 28 ± .25% |
| Potassium chloride | 2 ± .25% |
| (Poly)vinyl pyrrolidone | 1.5 ± .25% |

*AMPS is a trademark of The Lubrizol Corporation

In such formulation, the cross-linking copolymer comprises sodium 2-acyrylamido-2-methylpropanesulfonate and acrylic acid.

In contemplated embodiments, the hydrogel layer 16 may be provided to have a thermal conductivity of at least about 1.9 cal/hr-cm-° C., and preferably between about 1.9 cal/hr-cm-° C. and 2.37 cal/hr-cm-° C. Further, in various arrangements film layer 15 may be provided to have a thermal conductivity of between about 3.44 cal/hr-cm-° C. and 4.3 cal/hr-cm-° C.

In some implementations, the adhesive surface of the hydrogel layer may have a tack strength of between about 20 g and 65 g, as determined according to ISO 9665:1998(E).

In contemplated embodiments, the hydrogel layer may have a thickness of between about 0.018" and 0.04". More particularly, the hydrogel layer may have a thickness of between about 0.022" and 0.032".

In some implementations, the base member 14 may be defined by a closed foam material (e.g. a polymer foam material) that is heat pressed to form the rib members 14a and projections 14b. The film layer 15 may comprise a heat activatable film (e.g. a polymer material) that may be sealably bonded via a heat lamination process about its periphery to the periphery of the base member 14. Further, the heat lamination process may bond the film layer 15 to interfacing top surfaces of the rib members 14a, and optionally to interfacing top surfaces of the projections 14b.

In some embodiments, the removable liner layer 17 may be provided to peel away from adhesive surface 16a. In that regard, successive portions of the liner layer 17 may be pulled away from adhesive surface 16a to allow for successive adhesive positioning of different portions of adhesive surface 16a at a patient skin region.

Figure 5:
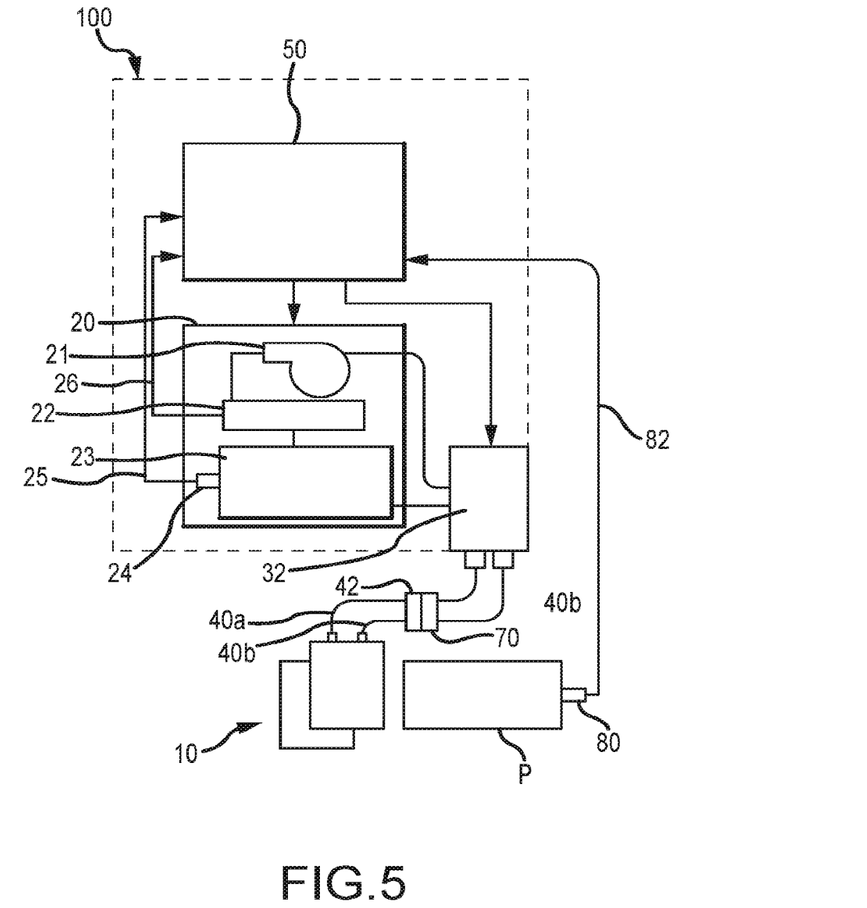
FIG. 5 is a schematic illustration of a system embodiment that includes the medical pad embodiment of FIG. 1.

FIG. 5 schematically illustrates one embodiment of a system 1 for patient temperature control. The system 1 may include a controller 50 for providing output signal 52 for use in the operation of a fluid conditioning assembly 20, so as to cool, optionally warm, and circulate thermal exchange fluid through one or more medical pad(s) 10.

The fluid conditioning assembly 20 may include a fluid pump 21 for circulating the thermal exchange fluid to a heat exchanger 23 for passage to a fluid coupling interface 30 and pad(s) 10. In one implementation, the controller 50, fluid conditioning assembly 20, and fluid coupling interface 30 may be supportably interconnected to a first support structure 100.

As noted, controller 50 may provide output signals for use in the operation of fluid conditioning assembly 20. More particularly, output signals 52 may include a signal for use in controlling the speed and/or duty cycle of the fluid pump 21 and a signal for controlling a cooling rate of the heat exchanger 23, and optionally, for controlling a warming rate of the heat exchanger 23. For example, the output signals 52 may include a signal for controlling a duty cycle of heat exchanger 23 and/or for controlling a magnitude of fluid thermal exchange provided by heat exchanger per time unit of operation.

In turn, the output signals 52 may be provided to control thermal exchange between the circulated fluid and a patient P via pad(s) 10. For example, the rate of thermal exchange between the circulated fluid and the patient P may be controlled so as to achieve a desired degree of patient temperature cooling for induced hypothermia and optional patient temperature warming to achieve normothermia.

To generate the output signals 52, the controller 50 may be provided to utilize one or a number of signals provided by one or more sensors comprising system 1. In particular, system 1 may include at least a first fluid temperature sensor 24 for sensing a temperature of the circulated fluid and providing a first fluid temperature signal 25 indicative thereof to controller 10. The first fluid temperature sensor 24 may be provided as part of the fluid conditioning assembly 20 and disposed to sense a temperature of the circulated fluid to be supplied through fluid coupling interface 30 to pad(s) 10. Additionally, controller 10 may be further provided to receive a patient temperature signal 82 from a patient temperature sensor 80, wherein the patient temperature signal is indicative of a sensed temperature of a patient P (e.g., a patient core body temperature).

Optionally, the fluid conditioning system 20 may also include a flow meter sensor 22 for measuring a flow rate of the circulated fluid (e.g., between the pump 21 and heat exchanger 22) and providing a flow rate signal 26 indicative thereof to controller 10, and a second fluid temperature sensor (not shown in FIG. 1) for sensing a temperature of the circulated fluid returning from thermal exchange module 40 (e.g., upstream of pump 21) and providing a second fluid temperature signal indicative thereof to controller 10. The flow rate signal 26 and/or second fluid temperature signal may also be utilized by controller 10 to generate one or more of the output signals 12a.

As shown, the fluid coupling interface 30 may be provided for selective fluid interconnection with one or more medical pad(s) 10 that may be utilized for thermal exchange with a patient P. For purposes of fluidly interconnecting fluid circulation lines 40a, 40b with fluid conditioning assembly 20, the connecter 42 may be configured for selective connection to and disconnection from a compatible connecter 70 provided on a reusable hose assembly that is interconnectable to and disconnectable from fluid at interface 30. In that regard, connectors may be employed as taught in U.S. Pat. No. 6,802,855, hereby incorporated by reference in its entirety.

Figure 6:
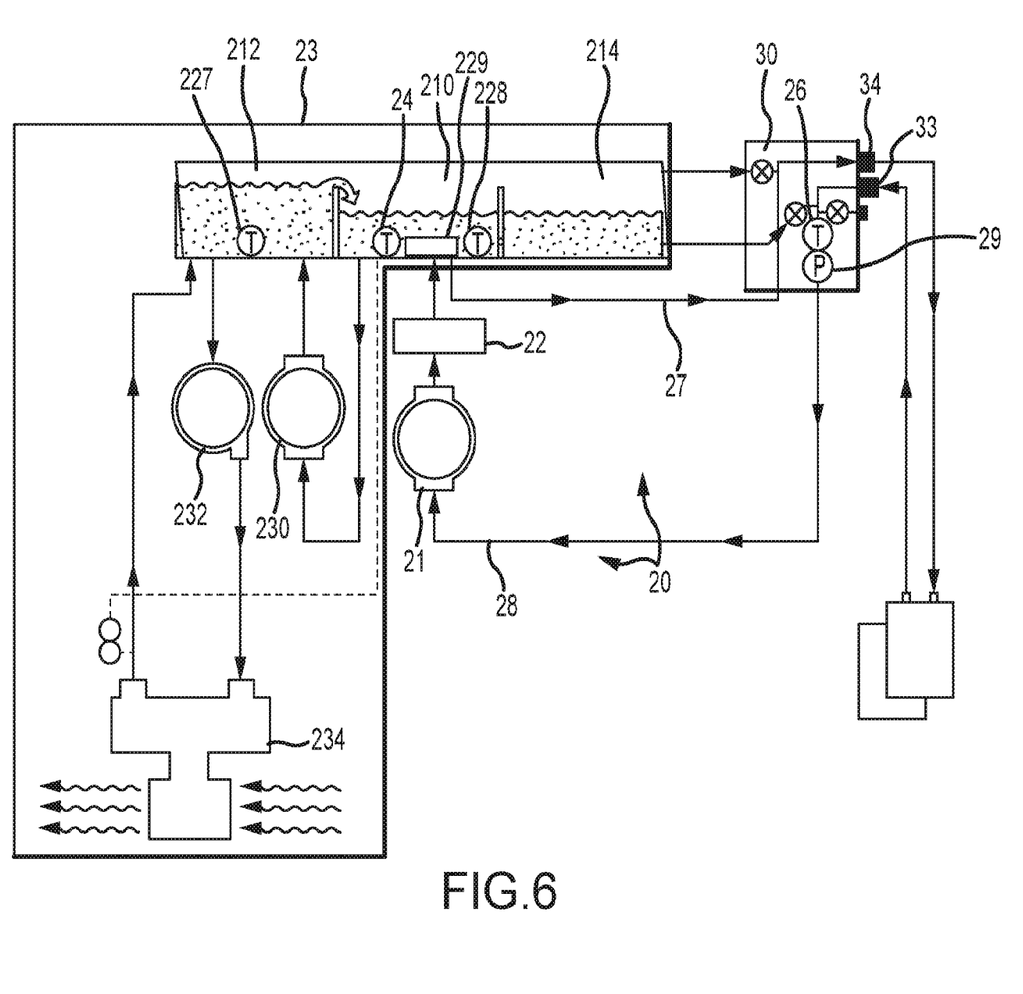
FIG. 6 is a schematic illustration of a fluid conditioning assembly of the system embodiment of FIG. 5.

FIG. 6 illustrates an embodiment of a fluid conditioning assembly 20 for use in the system embodiment of FIG. 5. As shown, fluid conditioning assembly 20 includes fluid pump 21 for pumping fluid through a flow meter 22 in to heat exchanger 23. Upon operation of fluid pump 21, fluid may be drawn from heat exchanger 23 through outlet line 27, through an outlet port 34 of fluid coupling interface 30, through the fluidly interconnected medical pad(s) 10, through inlet port 33 of fluid coupling interface 30, and through inlet line 28. As may be appreciated, the described operation may advantageously establish a negative pressure in medical pad(s) 10 to draw the circulated fluid therethrough. By way of example, a negative pressure of between about −0.5 psi and −10 psi may be provided.

Heat exchanger 23 may include a circulation tank 210 to receive the circulated fluid from fluid pump 21. In order to provide for an adequate amount of fluid, heat exchanger 23 may also optionally include a supply tank 214 for containing fluid that may flow into circulation tank 210 as needed in order to maintain a predetermined minimum amount of fluid in circulation tank 210 for flow in the described arrangement.

Heat exchanger 23 may further include a chiller tank 212 and a mixing pump 230 for pumping fluid from within circulation tank 210 into chiller tank 212. Additionally, heat exchanger 23 may include a chiller pump 232 and an evaporator/chiller 234, wherein upon operation of chiller pump 233 fluid may be pumped from chiller tank 212 through evaporator/chiller 234 and back into chiller tank 212 to yield cooling of fluid within chiller tank 212. In turn, fluid contained within chiller tank 212 may flow back into circulation tank 210 (e.g., by flowing over a barrier), wherein the fluid contained in circulation tank 210 may be cooled to a desired temperature via operation of mixing pump 230, chiller pump 232, and evaporator/chiller 234.

In that regard, operation of mixing pump 230, chiller pump 232, and evaporator/chiller 234 may be controlled by the output signals 52 of controller 50. As described above, the output signals 52 may be generated by controller 50 utilizing the first temperature signal 25 provided by first temperature sensor 24. As shown in FIG. 6 the first temperature sensor 24 may be located to sense the temperature of the fluid in circulation tank 210.

As further shown in FIG. 6, a second fluid temperature sensor 26 may be provided downstream of inlet port 33 to sense the temperature of the circulated fluid that is returned from the pad(s) 10. The second fluid temperature sensor 26 may provide a second temperature signal to controller 50 indicative of the sensed temperature for use in generation of output signals 52. Further, a third fluid temperature sensor 227 may be provided to sense the temperature of fluid within chiller tank 212 and provide a third temperature signal indicative of the sensed temperature. In turn, the third temperature signal may be utilized by controller 50 to generate output signals 52.

To provide redundancy in relation to the first fluid temperature sensor 24, a fourth fluid temperature sensor 228 may also be provided within circulation tank 210 to provide a fourth temperature signal indicative of the sensed temperature for redundant potential usage by controller 50 in generating output signals 52.

In the arrangement illustrated in FIG. 6, a fluid pressure sensor 28 may also be provided to sense the pressure of the circulated fluid returning from medical pad(s) 10. In turn, the pressure sensor 28 may provide a pressure signal to controller 50 indicative of the sensed pressure. In turn, controller 50 may utilize the pressure signal to generate output signals 52 provided to fluid pump 21, e.g., to control the speed of fluid pump 21 to provide for a desired negative pressure within the medical pad(s) 10.

With further reference to FIG. 6, heat exchanger 23 may include a heater 229 for selective heating of the fluid contained in circulation tank 210. In that regard, heater 229 may be provided to receive output signals 52 from controller 50 to provide a desired degree of heating to the fluid in circulation tank 210. As may be appreciated, operation of heater 229 may be utilized to heat the circulated fluid so as to effect patient rewarming in various embodiments.

Figure 7:
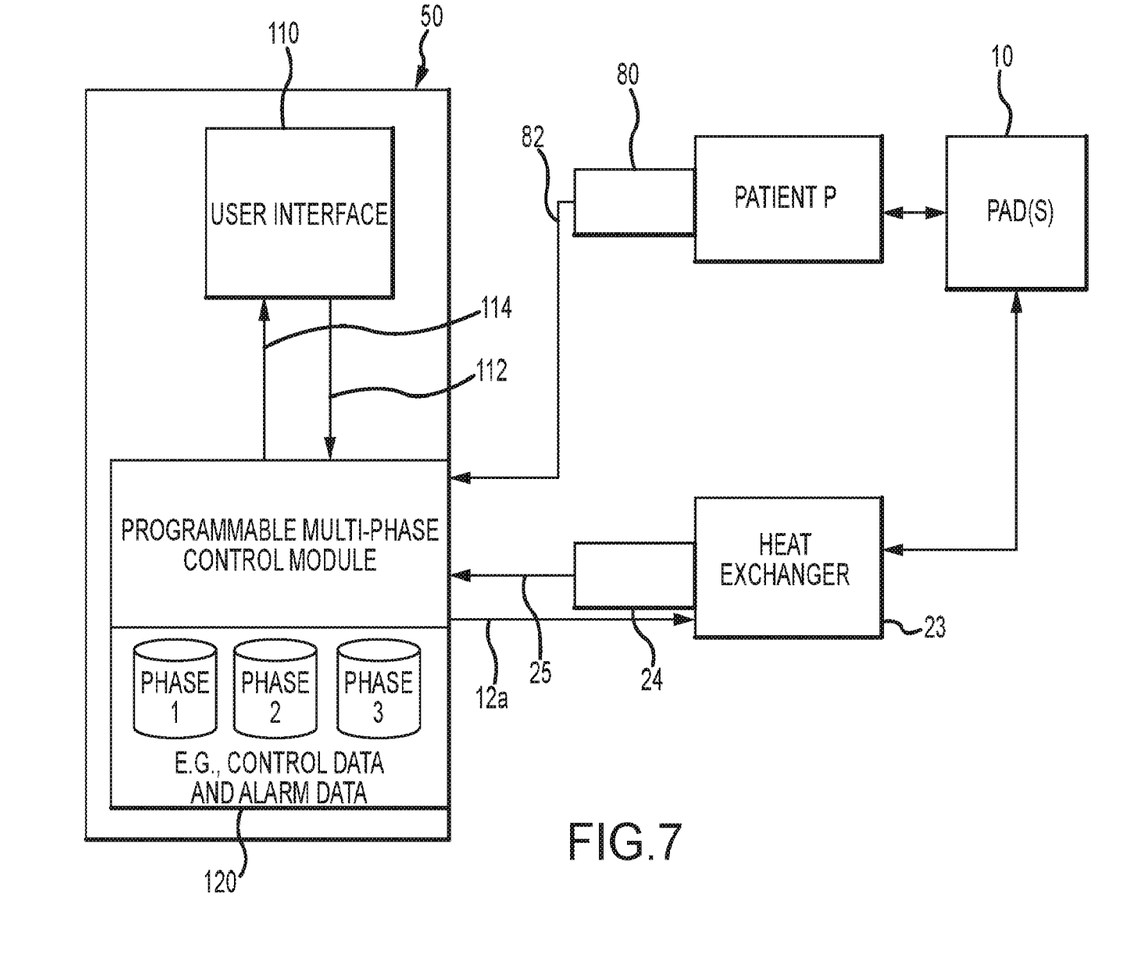
FIG. 7 is a schematic illustration of an embodiment of a controller of the system embodiment of FIG. 5.

FIG. 7 illustrates one embodiment of a controller 50. The controller 50 may be computer-based (e.g., a microprocessor) and may include a programmable control module 120 and a user interface 110 for receiving user control input and for providing corresponding signals 112 to the programmable control module 120. User interface 110 may be further adapted to receive signals 114 from the programmable control module 120 for use in the display of control and measured data and for operative, interactive interface with a user at user interface 110.

The programmable control module 120 may be provided to store control data (e.g., via a computer readable medium) and generate signals in corresponding relation to a plurality of different temperature control phases. In that regard, the programmable control module may comprise control logic for utilizing the control data to provide output signals to the heat exchanger 23 and/or the fluid pump 21, wherein the temperature of the circulated fluid is controlled in a predetermined manner for each of the plurality of different temperature control phases.

Additionally or alternatively, the programmable control module 120 may be provided to facilitate the establishment of one or more programmed protocols that each comprise control data for use in the control of each of the plurality of temperature control phases. By way of example, a given protocol may comprise control data that includes target patient temperature data for each of a plurality of treatment phases. Further, for one or more of the phases, the protocol may comprise control data comprising a set duration for thermal treatment. As may be appreciated, the user interface 110 may be adapted for use in receiving user input to establish the control data corresponding with each of the plurality of different patient temperature control phases on a protocol-specific basis.

For each given protocol the programmable control module 120 may provide output signals 52 to at least the heat exchanger 23, and optionally to fluid pump 21, on a phase-specific basis. In turn, thermal exchanger 23 may be provided to responsively change the temperature of the circulated fluid to affect a desired thermal exchange with a patient, e.g., to cool, maintain the temperature of, or warm a patient via contact thermal exchange via contact pad(s) 90. For example, and as noted above, heat exchanger 23 may comprise various componentry which operate to change the temperature of the circulated fluid in corresponding relation to control signals 52 output from the programmable control module 120.

As discussed above, system 1 may comprise a first fluid temperature sensor 24 for sensing the temperature of the circulated fluid on an ongoing basis and providing a corresponding first fluid temperature signal 25 to the controller 50. Further, patient temperature sensor 80 may be provided to sense the temperature of the patient P on an ongoing basis and provide corresponding signal 82 to the controller 50. In turn, the signals may be employed by the programmable control module 120, together with control data and preset algorithms, to generate (e.g., via the processor logic) the control signals 52 provided to heat exchanger 23, so as to yield the desired temperature of the circulated fluid (e.g., on a single phase or phase specific basis).

In one approach, the control data for a first phase of the plurality of different control phases may be established so that, during the first phase, the circulated fluid may be cooled to so that the patient reaches an established target patient temperature (e.g., corresponding with induced hypothermia). For such purposes, the controller 50 may utilize a patient temperature signal 82 as referenced above to determine whether or not and when a patient has reached the established target patient temperature (e.g., by comparison of the corresponding patient temperature to the established target patient temperature) and to provide output signals 52 to the heat exchanger 23 and/or fluid pump 21 responsive thereto. In one implementation, the circulated fluid may be cooled at a predetermined rate (e.g., a predetermined maximum rate) to cool a patient to the established target patient temperature as rapidly as possible (e.g., within predetermined system limits).

Optionally, the control data for the first phase of the plurality of different control phases may further comprise an established duration measure, wherein once the established target patient temperature is reached the patient is maintained at the established target patient temperature for any remaining portion of the established duration measure. Alternatively, the control data for a second phase of the plurality of different control phases may be established so that, during the second phase, the circulated fluid may be maintained at a temperature so that, via thermal exchange at medical pad(s), the patient is maintained at the established target patient temperature for an established duration of the second phase. Again, for such purposes, the controller 10 may utilize a patient temperature signal 82, as referenced above (e.g., to compare the corresponding patient temperature to the established target patient temperature) and to provide output signals 52 to the heat exchanger 23 and/or fluid pump 21 responsive thereto.

In further conjunction with the described approach, the control data for an additional phase after the first phase (e.g., a second phase or a third phase of the plurality of different control phases) may be established so that, during such phase, the circulated fluid may be warmed (e.g., at a predetermined rate) so that the patient reaches another established target patient temperature (e.g., corresponding with normothermia), and optionally, so that once such another established target patient temperature is reached, the patient is maintained at the another established target patient temperature for any remaining balance of an established duration of the additional phase or until the thermotherapy procedure is manually terminated by a user. For such purposes, the controller 50 may again utilize a patient temperature signal 82, as referenced above (e.g., to compare the corresponding patient temperature to the another established target patient temperature), and to provide output signals 52 to the heat exchanger 23 and/or fluid pump 21 responsive thereto.

As noted, the controller may comprise a user interface 110 for receiving user input and providing user control signals, wherein the control logic of the programmable processor control module 110 utilizes the user control signals together with the control data to provide the output signals 52. The user interface 110 may be further provided to establish and modify the control data stored by the programmable control module.

In some arrangements, the programmable control module may be operable to store at least two protocols comprising corresponding, different control data. In turn, the user interface 110 may be employable by user to select either of the two protocols for use by the programmable control module in generating the output signals.

Optionally, the user interface 110 may be provided to include a graphic display to visually present a plot of a target patient temperature adjustment rate that is based on the stored control data for a plurality of different temperature control phases. Further, the graphic display may be operable to display a plot of a sensed patient temperature (e.g., as sensed by the patient temperature sensor) in corresponding time relation to the plot of the target patient temperature adjustment rate. Further, the graphic display may be operable to display a plot of a sensed temperature of the circulated fluid (as sensed by the first fluid temperature sensor) in corresponding time relation to the plot of the target patient temperature adjustment rate.

In relation to one example of system 1, the fluid conditioning assembly 20 may utilize the Arctic Sun 5000 Temperature Management System product of Medivance, Inc., located in Louisville, Colorado, USA.

Figure 8:
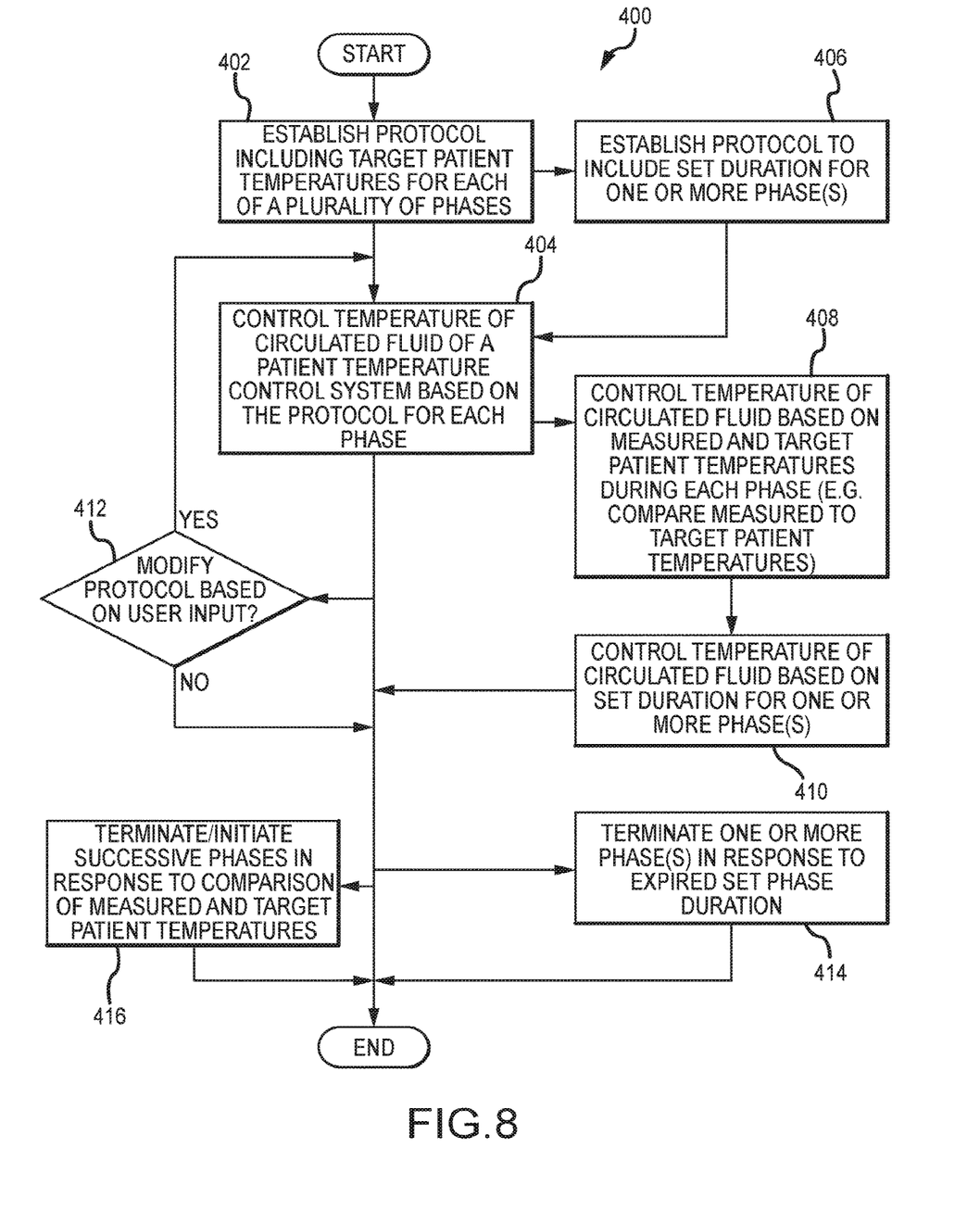
FIG. 8 illustrates steps of a method embodiment utilizing the system embodiment of FIGS. 5-7.

FIG. 8 illustrates one embodiment of a method 400 for controlling the temperature of a patient via control of the temperature of the circulated fluid in a multi-phase temperature control system. As illustrated, the method 400 may include an initial step 402 of establishing a protocol that includes target patient temperatures for a plurality of different temperature control phases (e.g., two or more non-overlapping phases having different patient temperature exchange objectives). Such phases may be successive in time and/or spaced in time. The establishment of a protocol may be achieved via use of the programmable control module 120 and operatively interconnected user interface 110 of FIG. 3.

By way of example, the protocol may be established to include target patient temperatures for at least three phases. Such an approach facilitates a procedure in which a patient is cooled to a first target patient temperature in a first phase of therapy, maintained at or within a predetermined range of a second target patient temperature during a second phase (e.g., equal or different than the first target temperature), and warmed to a third target patient temperature during a third phase. In other embodiments, following a third phase of therapy it may be desirable to establish a fourth target patient temperature for use in temperature control during a fourth phase of therapy.

The method may further include a step 404 of controlling the temperature of the circulated fluid based on the protocol for each of the plurality of phases, e.g., via control of the heat exchanger 23 via output signals 52 to control the temperature of the circulated fluid of FIGS. 5-7. In that regard, the protocol may be further established at step 406 so as to include a set duration for one or more of the phases, e.g., via use of a programmable control module 120 and user interface 110 of FIG. 3. In turn, the controlling step 404 may be carried out during such phase(s) for a duration(s) that corresponds with the set duration.

In one approach, the controlling step 404 may be carried out in step 408 for each phase by controlling the temperature of the circulated fluid based upon a sensed patient temperature and the target patient temperature for such phase, e.g., via use of a patient temperature signal 82 from patient temperature sensor 80 by the programmable control module 120 of FIG. 1. By way of example, the patient temperature may be sensed on an ongoing basis during a given phase and compared to the corresponding target patient temperature for such phase. Based upon such comparison, system 1 may provide for cooling and/or heating of the circulated fluid according to any of a plurality of pre-established algorithms, e.g., via control of the heat exchanger 23 by the programmable multi-phase control module 120 of controller 50 of FIG. 5.

In one approach, a control algorithm may provide for simply turning on/off the cooling/heating componentry of the heat exchanger 23 of system 1 (e.g., evaporator/chiller 234, chiller pump 232, and mixing pump for fluid cooling, and heater 229 for fluid heating) in intervals that depend upon a degree of difference reflected by comparison of the sensed patient temperature and target patient temperature. In another approach, a control algorithm may provide for controlling an output magnitude of the cooling/heating componentry of the heat exchanger 23 of system 1 (e.g., evaporator/chiller 234, chiller pump 232, and mixing pump for fluid cooling, and heater 229 for fluid heating) based upon a degree of difference reflected by comparison of the measured patient temperature and target patient temperature.

In another approach, the controlling step 404 may be completed as step 410 for a given phase by controlling the temperature of a thermal exchange medium based upon a sensed patient temperature, an established target patient temperature for such phase, and an established set duration for such phase. For example, utilization of the noted parameters accommodates the determination and control use of a target patient temperature adjustment rate for the phase, wherein gradual patient cooling/warming over a desired time period may be facilitated.

In yet another approach, one or more sensed circulated fluid temperature(s) (e.g., as sensed by first temperature sensor 23 and optionally second temperature sensor 26) may be employed together with a sensed patient temperature (e.g., as sensed by patient temperature sensor 80) and established target patient temperature (e.g., comprising control data stored at programmable control module 110) to control the heating/cooling of the circulated fluid. Such an approach may yield enhanced system response.

The illustrated method 400 may further provide for modification of a given protocol based on user input at step 412, e.g., via user input at the user interface 110 of FIG. 7. In this regard, a modified protocol may be employed for the remaining duration of a modified phase(s) and for any phase(s) that have not yet been initiated.

In the illustrated method, a given phase may be automatically terminated at step 414 by expiration of a corresponding set duration included within the programmed protocol for such phase. In that regard, the termination of a given phase may generally correspond with a change in the mode (e.g., cooling or heating) or a change in the magnitude of thermal exchange between the circulated fluid and a patient.

Method 400 may also provide for the termination and initiation of successive phases at step 416 in response to a comparison of a sensed patient temperature and a target patient temperature. That is, upon determining that a target patient temperature has been reached during a given phase (e.g., via comparison of a sensed patient temperature and a target patient temperature for an initial phase of treatment), such phase may be automatically terminated and a successive phase automatically initiated. Alternatively and/or additionally, the method 400 may also provide for the termination and initiation of successive phases in response to the expiration of a set duration for a first one of the two successive phases. The automatic phase termination/initiation features may be selectively established by a user for a given protocol on a phase-specific basis.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed is:

1. A method for making a medical pad for contact and thermal exchange with a patient, comprising:
   providing a fluid circulation layer for containing a thermal exchange fluid circulatable therethrough;
   connecting a first port to the fluid circulation layer for circulating the thermal exchange fluid into the fluid circulation layer;
   connecting a second port to the fluid circulation layer for circulating the thermal exchange fluid out of the fluid circulation layer; and
   adding a hydrogel layer to the fluid circulation layer so that the hydrogel layer extends across one side of the fluid circulation layer to define an adhesive surface for adherence to a patient's skin, the hydrogel layer including an ultraviolet light-cured composition, wherein:
      the ultraviolet light-cured composition comprises:
         a cross-linking copolymer in an amount of between about 25% to 30% by weight of the ultraviolet light-cured composition;
         water in an amount of between about 25% to 35% by weight of the ultraviolet light-cured composition; and
         glycerol in an amount of between about 27.5% to 32.5% by weight of the ultraviolet light-cured composition; and the hydrogel layer has a thermal conductivity of between about 1.9 cal/hr-cm-° C. and 2.37 cal/hr-cm-° C.

2. The method for making a medical pad according to claim 1, wherein the adhesive surface has a tack strength of between about 20 g and 65 g, as determined according to ISO 9665:1998(E).

3. The method for making a medical pad according to claim 1, wherein the hydrogel layer has a thickness of between about 0.018" and 0.04".

4. The method for making a medical pad according to claim 3, wherein the hydrogel layer has a thickness of between about 0.022" and 0.032".

5. The method for making a medical pad according to claim 1, wherein the fluid circulation layer is defined by:
a flexible film layer; and
a flexible base member interconnected to the flexible film layer for containing the thermal exchange fluid in an internal volume defined therebetween.

6. The method for making a medical pad according to claim 1, wherein the fluid circulation layer defines an internal volume having a geometric height across the fluid circulation layer of at least about 0.06".

7. The method for making a medical pad according to claim 6, wherein the fluid circulation layer comprises:
a flexible film layer; and
a flexible base member interconnected to the flexible film layer for containing the thermal exchange fluid in an internal volume defined therebetween, wherein the flexible base member includes a plurality of rib members interconnected to the flexible film layer.

8. The method for making a medical pad according to claim 7, wherein the plurality of rib members define a plurality of fluid flow channels through the fluid circulation layer.

9. The method for making a medical pad according to claim 8, wherein the plurality of fluid flow channels direct flow of a circulatable fluid flow between the first port and the second port.

10. The method for making a medical pad according to claim 7, wherein the plurality of rib members project from a base portion of the flexible base member by a projection distance that defines the geometric height of the fluid circulation layer.

11. The method for making a medical pad according to claim 10, wherein the projection distance is between about 0.06" and 0.1".

12. The method for making a medical pad according to claim 11, wherein the flexible base member further includes a plurality of offset projections that project from the base portion of the flexible base member by a distance substantially equal to the projection distance.

13. The method for making a medical pad according to claim 12, wherein the adhesive surface has a tack strength of between about 20 g and 65 g, as determined according to ISO 9665:1998(E).

14. The method for making a medical pad according to claim 13, wherein the hydrogel layer has a thickness of between about 0.022" and 0.032".

15. A method for making a medical pad for contact and thermal exchange with a patient, comprising:
providing a fluid circulation layer for containing a thermal exchange fluid circulatable therethrough;
connecting a first port to the fluid circulation layer for circulating the thermal exchange fluid into the fluid circulation layer;
connecting a second port to the fluid circulation layer for circulating the thermal exchange fluid out of the fluid circulation layer; and
adding a hydrogel layer to the fluid circulation layer so that the hydrogel layer extends across one side of the fluid circulation layer to define an adhesive surface for adherence to a patient's skin, the hydrogel layer including an ultraviolet light-cured composition, wherein:
the ultraviolet light-cured composition comprises:
a cross-linking copolymer in an amount of between about 15% to 30% by weight of the ultraviolet light-cured composition;
water in an amount of between about 15% to 40% by weight of the ultraviolet light-cured composition; and
glycerol in an amount of between about 25% to 35% by weight of the ultraviolet light-cured composition; and
the hydrogel layer has a thermal conductivity of between about 1.9 cal/hr-cm-° C. and 2.37 cal/hr-cm-° C.

16. The method for making a medical pad according to claim 15, wherein the fluid circulation layer is defined by:
a flexible film layer; and
a flexible base member interconnected to the flexible film layer for containing the thermal exchange fluid in an internal volume defined therebetween.

17. The method for making a medical pad according to claim 15, wherein a plurality of rib members define a plurality of fluid flow channels through the fluid circulation layer.

18. The method for making a medical pad according to claim 17, wherein the plurality of fluid flow channels direct flow of a circulatable fluid flow between the first port and the second port.

19. The method for making a medical pad according to claim 15, wherein the adhesive surface has a tack strength of between about 20 g and 65 g, as determined according to ISO 9665:1998(E).

* * * * *